United States Patent
Melker et al.

(10) Patent No.: US 7,052,468 B2
(45) Date of Patent: May 30, 2006

(54) METHOD AND APPARATUS FOR DETECTING ENVIRONMENTAL SMOKE EXPOSURE

(75) Inventors: Richard J. Melker, Gainesville, FL (US); Mark Gold, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 380 days.

(21) Appl. No.: 10/153,096

(22) Filed: May 22, 2002

(65) Prior Publication Data

US 2003/0004426 A1    Jan. 2, 2003

Related U.S. Application Data

(60) Provisional application No. 60/293,291, filed on May 24, 2001.

(51) Int. Cl.
*A61B 5/08* (2006.01)
*G01N 1/22* (2006.01)

(52) U.S. Cl. .................. 600/532; 600/529; 73/23.3
(58) Field of Classification Search ........ 600/529–543; 73/23.3; 422/84
See application file for complete search history.

(56) References Cited

U.S. PATENT DOCUMENTS

| | | | |
|---|---|---|---|
| 3,567,029 A | 3/1971 | Quame | |
| 3,608,546 A | 9/1971 | Shinn | |
| 3,649,199 A | 3/1972 | Littlejohn | |
| 3,792,272 A | 2/1974 | Harte et al. | |
| 3,877,291 A | 4/1975 | Hoppesch et al. | |
| 3,951,607 A | 4/1976 | Fraser | |
| 3,955,926 A | 5/1976 | Fischer | |
| 4,150,670 A | 4/1979 | Jewett et al. | |
| 4,202,352 A | 5/1980 | Osborn | |
| 4,215,409 A | 7/1980 | Strowe | |
| 4,312,228 A | 1/1982 | Wohltjen | |
| 4,314,564 A | 2/1982 | Albarda | |
| 4,334,540 A | 6/1982 | Preti et al. | |
| 4,346,584 A | 8/1982 | Boehringer | |
| 4,349,626 A | 9/1982 | Labows et al. | |
| 4,361,026 A | 11/1982 | Muller et al. | |
| 4,399,686 A | 8/1983 | Kindlund et al. | |
| 4,432,226 A * | 2/1984 | Dempster | 324/204 |
| 4,456,014 A | 6/1984 | Buck et al. | |
| 4,534,360 A | 8/1985 | Williams | |
| 4,734,777 A | 3/1988 | Okino et al. | |

(Continued)

FOREIGN PATENT DOCUMENTS

DE    19607646 A1    9/1997

(Continued)

OTHER PUBLICATIONS

U.S. Appl. No. 09/708,789, filed Nov. 8, 2000, Lampotang et al.

(Continued)

*Primary Examiner*—Charles Marmor
*Assistant Examiner*—Navin Natnithithadha
(74) *Attorney, Agent, or Firm*—Saliwanchik, Lloyd & Saliwanchik

(57) ABSTRACT

The present invention includes a method and apparatus for detecting exposure to environmental tobacco smoke by analyzing a sample of breath using electronic sensor technology, including surface acoustic-wave gas sensor technology. The method determines the presence and concentration of substance(s) (or a class of substances) indicative of environmental smoke exposure. Diagnostic software is used to identify substances where a stored library of signatures is compared to the signature obtained from the system. Signal processing and neural networks are preferably utilized in the analysis.

41 Claims, 5 Drawing Sheets

U.S. PATENT DOCUMENTS

| | | | |
|---|---|---|---|
| 4,735,777 A | 4/1988 | Mitsui et al. | |
| 4,772,559 A | 9/1988 | Preti et al. | |
| 4,796,639 A | 1/1989 | Snow et al. | |
| 4,868,545 A | 9/1989 | Jones | |
| 4,895,017 A | 1/1990 | Pyke et al. | |
| 4,938,928 A | 7/1990 | Koda et al. | |
| 4,992,244 A | 2/1991 | Grate | |
| 5,003,985 A | 4/1991 | White et al. | |
| 5,034,192 A | 7/1991 | Wrighton et al. | |
| 5,042,501 A | 8/1991 | Kenny et al. | |
| 5,060,506 A | 10/1991 | Douglas | |
| 5,071,770 A | 12/1991 | Kolesar, Jr. | |
| 5,081,871 A * | 1/1992 | Glaser | 73/863.23 |
| 5,082,630 A | 1/1992 | Partin et al. | |
| 5,094,235 A | 3/1992 | Westenskow et al. | |
| 5,111,827 A | 5/1992 | Rantala | |
| 5,137,692 A | 8/1992 | Fritz | |
| 5,145,645 A | 9/1992 | Zakin et al. | |
| 5,167,972 A | 12/1992 | Greenberg et al. | |
| 5,179,027 A | 1/1993 | Fisher | |
| 5,252,292 A | 10/1993 | Hirata et al. | |
| 5,296,706 A | 3/1994 | Braig et al. | |
| 5,303,575 A | 4/1994 | Brown et al. | |
| 5,317,156 A | 5/1994 | Cooper et al. | |
| 5,325,704 A | 7/1994 | Mariani et al. | |
| 5,351,522 A | 10/1994 | Lura | |
| 5,361,771 A * | 11/1994 | Craine et al. | 600/532 |
| 5,409,839 A | 4/1995 | Balestrieri et al. | |
| 5,425,374 A | 6/1995 | Ueda et al. | |
| 5,447,165 A | 9/1995 | Gustafsson | |
| 5,453,359 A | 9/1995 | Gargan et al. | |
| 5,465,608 A | 11/1995 | Lokshin et al. | |
| 5,466,700 A | 11/1995 | Batenhorst et al. | |
| 5,482,601 A | 1/1996 | Ohshima et al. | |
| 5,495,744 A | 3/1996 | Ueda et al. | |
| 5,501,212 A | 3/1996 | Psaros | |
| 5,528,924 A | 6/1996 | Wajid et al. | |
| 5,547,878 A | 8/1996 | Kell | |
| 5,558,083 A | 9/1996 | Bathe et al. | |
| 5,560,352 A | 10/1996 | Heim et al. | |
| 5,571,401 A | 11/1996 | Lewis et al. | |
| 5,573,005 A * | 11/1996 | Ueda et al. | 600/543 |
| 5,573,955 A | 11/1996 | Khanna et al. | |
| 5,605,612 A | 2/1997 | Park et al. | |
| 5,634,517 A | 6/1997 | Linden et al. | |
| 5,645,072 A | 7/1997 | Thrall et al. | |
| 5,716,852 A | 2/1998 | Yager et al. | |
| 5,756,879 A | 5/1998 | Yamagishi et al. | |
| 5,771,890 A | 6/1998 | Tamada | |
| 5,776,783 A | 7/1998 | Kell | |
| 5,783,154 A | 7/1998 | Althainz et al. | |
| 5,783,449 A | 7/1998 | Kuznetsov | |
| 5,795,787 A | 8/1998 | Silkoff et al. | |
| 5,801,297 A | 9/1998 | Mifsud et al. | |
| 5,826,577 A * | 10/1998 | Perroz et al. | 600/532 |
| 5,830,412 A | 11/1998 | Kimura et al. | |
| 5,861,254 A | 1/1999 | Schneider et al. | |
| 5,866,434 A | 2/1999 | Massey et al. | |
| 5,891,398 A | 4/1999 | Lewis et al. | |
| 5,900,552 A | 5/1999 | Chu et al. | |
| 5,918,257 A | 6/1999 | Mifsud et al. | |
| 5,925,014 A | 7/1999 | Teeple Jr. | |
| 5,928,167 A | 7/1999 | Wagner et al. | |
| 5,932,877 A | 8/1999 | Braig et al. | |
| 5,945,069 A | 8/1999 | Buehler | |
| 5,950,630 A | 9/1999 | Portwood et al. | |
| 5,954,685 A | 9/1999 | Tierney | |
| 5,958,896 A | 9/1999 | Renshaw et al. | |
| 5,962,335 A | 10/1999 | Katzman | |
| 5,971,937 A | 10/1999 | Ekstrom | |
| 5,996,586 A | 12/1999 | Phillips | |
| 6,007,775 A | 12/1999 | Yager | |
| 6,010,459 A | 1/2000 | Silkoff et al. | |
| 6,025,200 A | 2/2000 | Kaish et al. | |
| 6,057,162 A | 5/2000 | Rounbehler et al. | |
| 6,063,243 A | 5/2000 | Zettl et al. | |
| 6,067,167 A | 5/2000 | Atkinson et al. | |
| 6,074,345 A | 6/2000 | van Oostrom et al. | |
| 6,085,576 A | 7/2000 | Sunshine et al. | |
| 6,094,681 A | 7/2000 | Shaffer et al. | |
| 6,097,485 A | 8/2000 | Lievan | |
| 6,120,443 A | 9/2000 | Cohen-Laroque | |
| 6,131,571 A | 10/2000 | Lampotang et al. | |
| 6,136,801 A | 10/2000 | Kell | |
| 6,153,147 A | 11/2000 | Craig | |
| 6,180,414 B1 | 1/2001 | Katzman | |
| 6,186,977 B1 | 2/2001 | Andrews et al. | |
| 6,190,858 B1 | 2/2001 | Persaud et al. | |
| 6,203,814 B1 | 3/2001 | Fisher et al. | |
| 6,216,690 B1 | 4/2001 | Keitel et al. | |
| 6,221,026 B1 | 4/2001 | Phillips | |
| 6,234,006 B1 | 5/2001 | Sunshine et al. | |
| 6,237,397 B1 | 5/2001 | Shinar et al. | |
| 6,244,096 B1 * | 6/2001 | Lewis et al. | 73/23.2 |
| 6,248,078 B1 | 6/2001 | Risby et al. | |
| 6,251,082 B1 | 6/2001 | Rayburn | |
| 6,261,783 B1 | 7/2001 | Jayasena et al. | |
| 6,264,913 B1 | 7/2001 | Wagner | |
| 6,277,081 B1 | 8/2001 | Susi et al. | |
| 6,283,953 B1 | 9/2001 | Ayer et al. | |
| 6,303,316 B1 | 10/2001 | Kiel et al. | |
| 6,305,212 B1 | 10/2001 | Drzewiecki | |
| 6,312,390 B1 | 11/2001 | Phillips | |
| 6,319,724 B1 | 11/2001 | Lewis et al. | |
| 6,328,708 B1 | 12/2001 | Georgieff | |
| 6,341,520 B1 | 1/2002 | Satoh et al. | |
| 6,363,772 B1 | 4/2002 | Berry | |
| 6,387,329 B1 | 5/2002 | Lewis et al. | |
| 6,399,302 B1 | 6/2002 | Lannigan et al. | |
| 6,416,479 B1 * | 7/2002 | Seidman | 600/532 |
| 6,455,319 B1 | 9/2002 | Lewis et al. | |
| 6,467,333 B1 | 10/2002 | Lewis et al. | |
| 6,479,019 B1 | 11/2002 | Goldstein et al. | |
| 6,495,824 B1 | 12/2002 | Atkinson | |
| 6,511,453 B1 | 1/2003 | Georgieff | |
| 6,558,626 B1 | 5/2003 | Aker et al. | |
| 6,589,727 B1 | 7/2003 | Klenerman et al. | |
| 6,597,438 B1 | 7/2003 | Cabuz et al. | |
| 6,598,459 B1 | 7/2003 | Fu | |
| 6,599,253 B1 | 7/2003 | Baum et al. | |
| 6,599,281 B1 | 7/2003 | Struys et al. | |
| 6,620,800 B1 | 9/2003 | Roberts, II | |
| 6,631,333 B1 | 10/2003 | Lewis et al. | |
| 6,680,377 B1 | 1/2004 | Stanton et al. | |
| 6,727,075 B1 | 4/2004 | Fitzgerald et al. | |
| 6,755,783 B1 | 6/2004 | Cosentino et al. | |
| 2001/0021815 A1 | 9/2001 | Katzman et al. | |
| 2001/0041366 A1 | 11/2001 | Lewis et al. | |
| 2001/0046674 A1 | 11/2001 | Ellington | |
| 2001/0050228 A1 | 12/2001 | Jaeger | |
| 2001/0055544 A1 | 12/2001 | Copp | |
| 2002/0007249 A1 | 1/2002 | Cranley et al. | |
| 2002/0007687 A1 | 1/2002 | Zimmermann et al. | |
| 2002/0014236 A1 | 2/2002 | Dittmann et al. | |
| 2002/0017300 A1 | 2/2002 | Hickle et al. | |
| 2002/0034757 A1 | 3/2002 | Cubicciotti | |
| 2002/0068295 A1 | 6/2002 | Madou et al. | |
| 2002/0173729 A1 | 11/2002 | Viertio-Oja et al. | |
| 2002/0177232 A1 | 11/2002 | Melker et al. | |
| 2003/0004426 A1 | 1/2003 | Melker et al. | |
| 2003/0008407 A1 | 1/2003 | Fu | |
| 2003/0059820 A1 | 3/2003 | Vo-Dinh | |
| 2003/0087239 A1 | 5/2003 | Stanton et al. | |
| 2003/0119065 A1 | 6/2003 | Lin et al. | |

| 2003/0139681 A1 | 7/2003 | Melker et al. |
| 2003/0216660 A1 | 11/2003 | Ben-Oren et al. |
| 2004/0027246 A1 | 2/2004 | Aguglia |
| 2004/0101477 A1 | 5/2004 | Leyland-Jones |
| 2005/0065446 A1 | 3/2005 | Talton |

FOREIGN PATENT DOCUMENTS

| DE | 29902593 | | 8/1999 |
| EP | 0370151 | A1 | 5/1990 |
| EP | 0979997 | A1 | 2/2000 |
| GB | 829409 | | 3/1960 |
| GB | 2 309 166 | A | 7/1997 |
| GB | 2329245 | A | 3/1999 |
| JP | 08313407 | | 11/1996 |
| JP | 09196915 | A | 7/1997 |
| RU | 2104535 | C | 2/1998 |
| WO | WO 87/02773 | A1 | 5/1987 |
| WO | WO 92/10749 | A1 | 6/1992 |
| WO | WO 95/08113 | A1 | 3/1995 |
| WO | WO 95/31718 | A1 | 11/1995 |
| WO | WO 98/57145 | A1 | 12/1998 |
| WO | WO 99/12471 | A3 | 3/1999 |
| WO | WO 99/66304 | A1 | 12/1999 |
| WO | WO 00/25108 | A1 | 5/2000 |
| WO | WO 00/67820 | A1 | 11/2000 |
| WO | WO 0079243 | A1 | 12/2000 |
| WO | WO 01/34024 | A1 | 5/2001 |
| WO | WO 0193743 | A2 | 12/2001 |
| WO | WO 2002/079514 | A1 | 10/2002 |
| WO | WO 03/016901 | A1 | 2/2003 |
| WO | WO 03/045473 | A1 | 6/2003 |
| WO | WO 2004/065404 | A1 | 8/2004 |

OTHER PUBLICATIONS

Chandiok S. et al., "Screening for Bacterial Vaginosis: A Novel Application of Artificial Nose Technology", *Journal of Clinical Pathology*, 1997, vol. 50, pp. 790-791.

Dickinson T. et al., "Current Trends in 'Artificial-Nose' Technology" *Tib Tech*, 1998, vol. 16, pp. 250-258.

Fang, M. et al., "Detection of Organic Chemicals by SAW Sensor Array,", *Sensors and Actuators*, 1999, vol. B56, pp. 155-157.

Ganga-Zandzou, P.S. et al., "A 13C-urea breath test in children with Hellcobacter pylori infection: validity of the use of a mask to collect exhaled breath sample," *Acta. Paediatr.*, 2001, vol. 90, pp. 232-233.

Groves, W. et al., "Analyzing organic vapors in exhaled breath using a surface acoustic wave sensor array with preconcentration: Selection and characterization of the preconcentrator adsorbent," *Analytica Chirnica Acta*, 1998, vol. 371, pp. 131-143.

Miller E. et al., "Association Between Cigarette Smoking and Lipid Peroxidation in a Controlled Feeding Study" *Circulation*, 1997, vol. 96, No. 4, pp. 1097-1101.

Parry A.D. et al., "Leg Ulcer Odour Detection Identifies β-haemolytic Streptococcal Infection" *Journal of Wound Care*, 1995, vol. 4, No. 9, pp. 404-406.

Perri, F., "Diagnosis of Helicobacter pylori infection: which is the best test? The urea breath test," *Dig. Liver. Dis.*, 2000, vol. 32, Supplemental 3, pp. S196-198.

Phillips, M., "Breath Tests in Medicine" *Scientific American*, 1992, pp. 52-57.

Brody et al., "The Use of Aptamers in Large Arrays for Molecular Diagnostics," *Molecular Diagnosis*, 1999, pp. 381-388, vol. 4, No. 4, Churchill Livingstone.

Brody and Gold, "Aptamers as therapeutic and diagnostic agents," *Reviews in Molecular Biotechnology*, 2000, pp. 5-13, vol. 74, Elsevier Science B.V.

Stojanovic et al., "Aptamer=Based Folding Fluorescent Sensor for Cocaine", *J. Am. Chem. Soc.*, 2001, pp. 4928-4931, vol. 123, American Chemical Society.

Ballantine, D. S. et al., "Surface Acoustic Wave Devices for Chemical Analysis," *Anal. Chem.* (1989), vol. 61, No. 11, pp. 704A-712A.

Fisher et al. "A man-portable chemical sniffer utilizing Novel Fluorescent polymers for detection of ultra-trace concentrations of explosives emanating from landmines," *Nomadics Inc.* (2000), pp. 1-10.

Frauendorf et. al., "Detection of Small Organic Analytes by Fluorescing Molecular Switches,", *Bioorganic & Medicinal Chemistry 9*, (2001), pp. 2521-2524.

Fujita et al., "A Simple Method for Dectecting Plasma Propofol," *Anesth Analog.*, 2000, 90:1452-1454.

Grate, JW et al. "Determination of Partition Coefficients from Surface Acoustic Wave Vapor Senor Responses and Correlation with Gas-Liquid Chromatographic Partition Coefficients," *Anal. Chem.* (1998), vol. 60, pp. 869-875.

Hammon III, W. S. et al., "Forensic GPR: Finite-Difference Simulations of Responses From Buried Human Remains," *Journal of Applied Geophysics*, (2000), 45:171-186.

Hanson III, C.W. et al. "The use of a novel 'Electronic Nose' to diagnose the presence of intrapulmonary infection," *Anesthesiology* (1997), vol. 87, No. 3A, abstract A269.

Hong, C. et al., "Carbon Nanotube-Enhanced Electrochemical DNA Biosensor for DNA Hybridization Detection" (2003), *Anal. Bioanal. Chem.*, 375:287-293.

Huang et. al., "Depth of Anesthesia Estimating & Propofol Delivery System," Aug. 1, 1996, http://www.rpi.edu/~royr/roy_descpt.html.

Jayasena, "Aptamers: An Emerging Class of Molecules That Rival Antibodies in Diagnostics," *Clinical Chemistry*, 1999, 45(9):1628-1650.

Kenny, "Target-Controlled Infusions—Pharmacokinetic and Pharmacodynamic Variations," http://www.anaesthesiologie.med.uni-erlangen.de/esctaic97/a_kenny.htm.

Kuipers et al., "First-pass Lung Uptake and Pulmonary Clearance of Propofol," *Anesthesiology*, (1999), 91:1780-1787.

Liebich et al. "Volatile Substances in Blood Serum: a Profile Analysis and Quantitative Determination," *Journal of Chromatography* (1977), vol. 142, pp. 505-516.

Mueller et al. "Experience in mass spectrometric identification in acute poisoning," *Beitr. Diagn. Ther, Akuter. Intox., Vortr. Symp.* $4^{th}$ (1982), pp. 126-134, abstract only.

Pantarotto D. et al., "Synthesis, Structural Characterization, and Immunological Properties of Carbon Nanotubes Functionalized with Peptides" (2003), *J. Am. Chem. Soc.*, 125:6160-6164.

Pavlou and Turner. "Sniffing out the truth: Clinical Diagnosis Using the Electronic Nose," *Clin. Chem. Lab. Med.* (2000), vol. 38, No. 2, pp. 99-112.

Pilar Kraman, "Prescription Drug Diversion," *Trends Alert* provided by the Council of State Government at www.csg.org (Apr. 2004).

Rogers et al. "Fiber-optic biosensors based on total internal-reflection fluorescence," *American Chemical Society* (1992), Ch. 13, pp. 165-173.

Stuart, B. H. et al., "Studies of Adipocere Using Diffuse Reflectance Infrared Spectroscopy," *Vibrational Spectroscopy*, 24:233-242, (2000).

Stubbs, D. D. et al., "Investigation of Cocaine Plumes Using Surface Acoustic Wave Immunoassay Sensors," *Anal. Chem.*, 75:6231-6235, (2003).

Tracqui, A. et al. "Systematic Toxicological Analysis Using HPLC/DAD," *Journal of Forensic Sciences* (1995), vol. 40, No. 2, pp. 254-262.

U.S. Food and Drug Administration, "FDA White Paper, Protecting the Public Health: FDA Pursues and Aggressive Enforcement Strategy," www.fda.gov/oc/whitepapers/enforce.html (Jun. 30, 2003).

U.S. Food and Drug Administration, "New FDA Initiative to Combat Counterfiet Drugs," www.fda.gov/oc/initiatives/counterfeit/backgrounder.html (Jul. 2, 2004).

United States Department of Justice, "Review of the Drug Enforcement Administration's (DEA) Control of the Diversion of Controlled Pharmaceuticals," Report No. I-2002-010 www.usdoj.gov/oig/inspection/DEA/210/background.htm (Sep. 2002).

Wohltjen, H. et al. "Vapor Detection with Surface Acoustic Wave Microsensors," *Chemical Sensors and Microinstrumentation* (1989), pp. 157-175.

Vass, A., "Beyond the Grave—Understanding Human Decomposition," *Microbiology Today*, Nov. 2001, 28:190-192.

Vass, A. et al., "Decomposition Chemistry of Human Remains: A New Methodology for Determining the Postmortem Interval," *J. Forensic Sci.*,(2002), 47(3):542-553.

Vass, A. et al., "Detection of Buried Human Remains Using Bioreporter Fluorescence," U.S. Dept. of Energy Report, Y/NSP-726 (2001).

* cited by examiner

METHOD AND APPARATUS FOR DETECTING ENVIRONMENTAL SMOKE EXPOSURE

CROSS-REFERENCE TO A RELATED APPLICATION

This application claims the benefit of U.S. Provisional Application Ser. No. 60/293,291, filed May 24, 2001, incorporated herein by reference.

FIELD OF INVENTION

The present invention relates to the detection of environmental smoke exposure, and, more particularly, to a method and apparatus for the detection of environmental smoke exposure in exhaled breath utilizing a rapidly responding device.

BACKGROUND INFORMATION

The health risks related to tobacco smoking are well documented. It is the single most important preventable cause of death and disability in the U.S. and causes an estimated 450,000 deaths annually. Despite widespread dissemination of this information, a significant proportion of Americans (approximately 25%) continues to or starts smoking. Worldwide it is estimated that there are over 1.2 billion tobacco smokers. The result is a huge economic burden on the population. Of particular concern is mounting evidence that exposure to environmental tobacco smoke (ETS) is also a cause of significant morbidity and mortality. Children are particularly susceptible.

Numerous strategies are being implemented to reduce childhood exposure to ETS including prohibitions on smoking in day care settings, school, and public places. Relatively few strategies have focused on the main source of ETS (i.e., smoking in the home). Identifying children by history of parental smoking becomes less productive as the parents become more aware than their smoking could cause disease in those sharing the household. Furthermore, ongoing monitoring of progress has been limited by existing technology for identifying ETS exposure. One strategy that appears to be somewhat effective, has been implemented in California, the state that has been most aggressive at reducing risk associated with ETS. As part of a comprehensive program of tobacco control, behavioral counseling of ethnically diverse, low income populations on the effects of ETS on children has been implemented and shown to significantly reduce exposure. This, however, is a short-term and limited solution to the problem. Such a strategy could be enhanced by a convenient biological measurement that could be done by any parent or child anytime, daily or many times a week at home.

Unfortunately, large number of children remain at risk of respiratory diseases, such as asthma, due to household exposure. In some instances, where asthma attacks exacerbated by ETS have been life threatening, children have had to be removed from the environment. Clearly, no single strategy is going to prevent exposure to ETS anymore than strategies to reduce smoking are going to completely stop its use.

Because it is difficult to police tobacco use in the home and the resulting exposure to ETS, it is desirable to be able to detect exposure when children are seen by healthcare professionals. ETS screening, recommended by both the CDC and AAP, should be implemented as a standard addition to the pediatric or health department exam and become a fifth vital sign.

Several techniques are available to detect tobacco byproducts, (usually the nicotine metabolite, cotinine) in blood, urine and more recently in saliva. The association between the number of cigarettes smoked per day and saliva cotinine levels has been shown to be almost linear. Similarly, the size of the house that the child of the smoker lives in is inversely related to the degree of toxic exposure. Other measurement techniques include exhaled carbon monoxide (CO) and salivary thiocyanate.

To obtain a high degree of accuracy for studying tobacco smoking, a single biomarker may not be sufficient, because smoking is a discontinuous process. Exhaled CO is a good marker of short-term exposure, while combining its measurement with either thiocyanate or cotinine provides a high correlation with smoking status, and is more accurate than self-reporting CO measurement alone. A recent study showed that cotinine levels in non-smokers who have close friends or a spouse who smoke are 1.5 times higher than those whose friends/spouse are non-smokers.

Unfortunately, these techniques are costly, time consuming, require considerable cooperation by the subject and the results are not immediately available. This reduces their value for studying smoking and ETS in individual subjects, especially children. What is needed is an inexpensive device that can detect exposure to vapors in tobacco smoke in real time. The ability to distinguish smoking or ETS from the therapeutic use of nicotine as part of a discontinuation program would also be advantageous.

Furthermore, a recent study estimates that the economic burden to payers and society of maternal smoking during pregnancy and the first year of life ranges from $1142 to $1358 per child.

Accordingly, there is a need in the art for a tobacco smoke detector for determining the exposure of children to environmental tobacco smoke (ETS) (passive smoke, sidestream smoke, second-hand smoke). Such a device would be applicable for a wide range of research related to the effects of smoking and its complications. There is also a need in the art for a detector for environmental smoke exposure capable of being used at remote locations.

BRIEF SUMMARY OF THE INVENTION

The present invention solves the problems in the art by providing a method and apparatus for detecting environmental smoke exposure by providing a device for analyzing the patient's breath to confirm exposure to vapors in tobacco smoke. The method of the present invention can be used to monitor smoking behavior. For example, it can be used to monitor whether subjects are abstaining from smoking or continuing to smoke and whether children and adults are being exposed to environmental tobacco smoke. Many constituents of tobacco smoke are well known, several of which are carcinogens. A device designed to monitor tobacco smoke constituents in exhaled breath, as in the present invention, can be extremely valuable for research into the effect of tobacco smoke. Further, it can be used for monitoring compliance by parents in preventing exposure of their children, especially those with respiratory conditions that are exacerbated by tobacco smoke. A device based on polymer-coated SAW sensor technology has broad application in detecting tobacco smoke by-products both in the environment and in exhaled breath of smokers and non-smokers. This is extremely important as environmental tobacco smoke has been shown to cause significant morbidity and mortality in non-smokers. Among the byproducts of tobacco smoke are benzene and formaldehyde, both well known carcinogens.

Compounds to be tested for include, but are not limited to, ETS components (e.g., acetaldehyde, acetic acid, acetone, acrolein, 4-Amniobiphenol, ammonia, anatabine, aniline, benzene, benzanthracene, benzopryene, benzoic acid, gamma-butyrolactone, cadmium, carbon monoxide, carbonyl sulfide, catechol, cotinine, cyanide derivatives, dimethylamine, formaldehyde, formic acid, glycolic acid, Harman, hydrazine, hydrogen cyanide, hydroquinone, isoprene, methylamine, methyl chloride, 3-methylpyridine, 2-naphthylamine, nickel, nicotine, nitrogen oxides, N-Nitrosodiethanolamine, N-Nitrosodiethylamine, N-Nitrosodimethylamine, NNK, phenol, polonium-210, propionaldehyde, pyridine, quinoline, succinic acid, toluene, 2-Toluidine, 3-Vinylpyridine, xylene, and Zinc).

Preferably, the patient's breath is analyzed to confirm exposure to vapors in tobacco smoke by sensor technology selected from semiconductor gas sensor technology, conductive polymer gas sensor technology, surface acoustic wave gas sensor technology, aptamers (aptamer biosensors), and amplifying fluorescent polymer (AFP) sensors. The sensor technology produces a unique electronic fingerprint to characterize exposure to vapors in tobacco smoke such that the presence and concentration is determined.

In the monitoring system, vapor concentration measurements of smoke vapors (analytes) are made by detecting the adsorption of molecules onto the surface of a SAW sensor coated with a polymer thin film to provide selectivity and sensitivity to different analytes. The SAW is inserted as an active feedback element in an oscillator circuit. A frequency counter measures the oscillation frequency, which corresponds to the resonant frequency of the SAW sensor. The response of the SAW sensor to the analyte is measured as a shift in the resonant frequency of the SAW sensor. This configuration requires an oscillator circuit, the coated SAW sensor, and a frequency counter, all of which may be housed on a small printed circuit board.

In alternate embodiments, the patient's breath is analyzed to confirm the presence of the vapors by a spectrophotometer or a mass spectrometer.

The method further includes the step of recording data resulting from analysis of the patient's breath. The method further includes the step of transmitting data resulting from analysis of the patient's breath.

In operation, the analysis of the patient's breath includes comparing the vapors sensed in the patient's breath with a predetermined signature profile of the vapors. The predetermined signature profile is associated with a specific compound or a class of compounds. The method may further include the step of capturing the patient's breath in a vessel prior to analysis as well as dehumidifying the patient's breath prior to analysis in a manner well known in the art. Breath can be captured from the patient's mouth or nose. The data resulting from analysis of the patient's breath preferably includes vapor concentration. In certain instances, such as during a treatment program, a baseline spectrum for the patient may be identified. In a further embodiment, the analysis includes detecting exhalation of the patient's breath with a sensor.

The preferred device of the present invention includes (a) a sensor having a surface exposed to the patient's breath and/or airway and comprising a material selectively absorptive of a chemical vapor or group of vapors; and (b) an analyzer, coupled to the sensor, for producing an electrical signal indicative of the presence of the vapors. The analyzer is further operative to determine the approximate concentration of the vapors. The sensor is preferably a surface acoustic wave device, such as that disclosed in pending U.S. application Ser. No. 09/708,789 entitled "Marker Detection Method and Apparatus to Monitor Drug Compliance" of which applicant is a co-inventor, the description of which is incorporated herein by reference. The sensor device disclosed in U.S. Pat. No. 5,945,069 may also be utilized. The device detects a target substance (tobacco smoke) in expired breath having the following components: (a) a surface-acoustic wave sensor capable of detecting the presence of the target substance in expired breath, wherein the sensor responds to the target substance by a shift in the resonant frequency; (b) an oscillator circuit having the sensor as an active feedback element; (c) a frequency counter in communication with the oscillator circuit to measure oscillation frequency which corresponds to resonant frequency of the sensor; and (d) a processor for comparing the oscillation frequency with a previously measured oscillation frequency of the target substance and determining presence and concentration of the target substance therefrom.

In an alternate embodiment, the device detects a target substance (tobacco smoke) in expired breath having the following components: (a) a sensor having an array of polymers capable of detecting the presence of the target substance in expired breath, wherein the sensor responds to the target substance by changing the resistance in each polymer resulting in a pattern change in the sensor array; (b) a processor for receiving the change in resistance, comparing the change in resistance with a previously measured change in resistance, and identifying the presence of the target substance from the pattern change and the concentration of the substance from the amplitude. The processor can include a neural network for comparing the change in resistance with a previously measured change in resistance to find a best match.

The invention also includes a method of determining the rate of washout of a target substance (tobacco smoke) in expired breath by (a) obtaining a sample of expired breath at a first interval; (b) analyzing the sample with sensor technology to determine the concentration of the substance; (c) obtaining at least one additional sample of expired breath at a later interval; (d) analyzing said additional sample with sensor technology to determine the concentration of said substance; and (e) comparing the concentration of the first sample with the concentration of additional samples to determine rate of washout of the target substance.

The device may also include a means for receiving air exhaled by the patient. Preferably, the device comprises sensor technology selected from semiconductor gas sensor technology, conductive polymer gas sensor technology, or surface acoustic wave gas sensor technology.

Accordingly, it is an object of the present invention to detect vapors, such as environmental tobacco smoke, by methods including, but not limited to, sensor technology (e.g., silicon chip technology).

It is a further object of the present invention to provide a reporting system capable of tracking results and alerting healthcare personnel, and/or in some instances health officials.

The advantages of the invention are numerous. First and foremost, the exhaled breath detector for ETS can have broad implications for ETS research. A resulting advantage of the ability to rapidly detect ETS through a simple and efficient system is the ability to allow for evaluation of the relationship of ETS to asthma and other respiratory diseases.

The subject technology for the present invention is inexpensive and potentially has broad medical application for detecting a wide range of compounds in exhaled breath. The potential use for the device at remote locations in conjunction with other medical devices is considerable. The device could be used in the home or the workplace. In conjunction with data acquisition technology, the detector and other medical devices such as spirometers could be used and the data stored and relayed to researchers.

Present techniques to monitor adherence with abstinence regimens or prevention of exposure of children require testing of blood, urine, or saliva. The present invention is extremely valuable for measurements in children as it is inconvenient and sometimes difficult to obtain other samples. The device may be used in conjunction with a communication system, which would allow storage of the data at a central location where it could then be communicated to appropriate healthcare providers or researchers.

Further objects and advantages of the present invention will become apparent by reference to the following detailed disclosure of the invention and appended drawings.

All documents and publications cited herein are incorporated herein by reference in their entirety to the extent they are not inconsistent with the explicit teachings set forth herein.

DETAILED DESCRIPTION OF THE INVENTION

Figure 1:
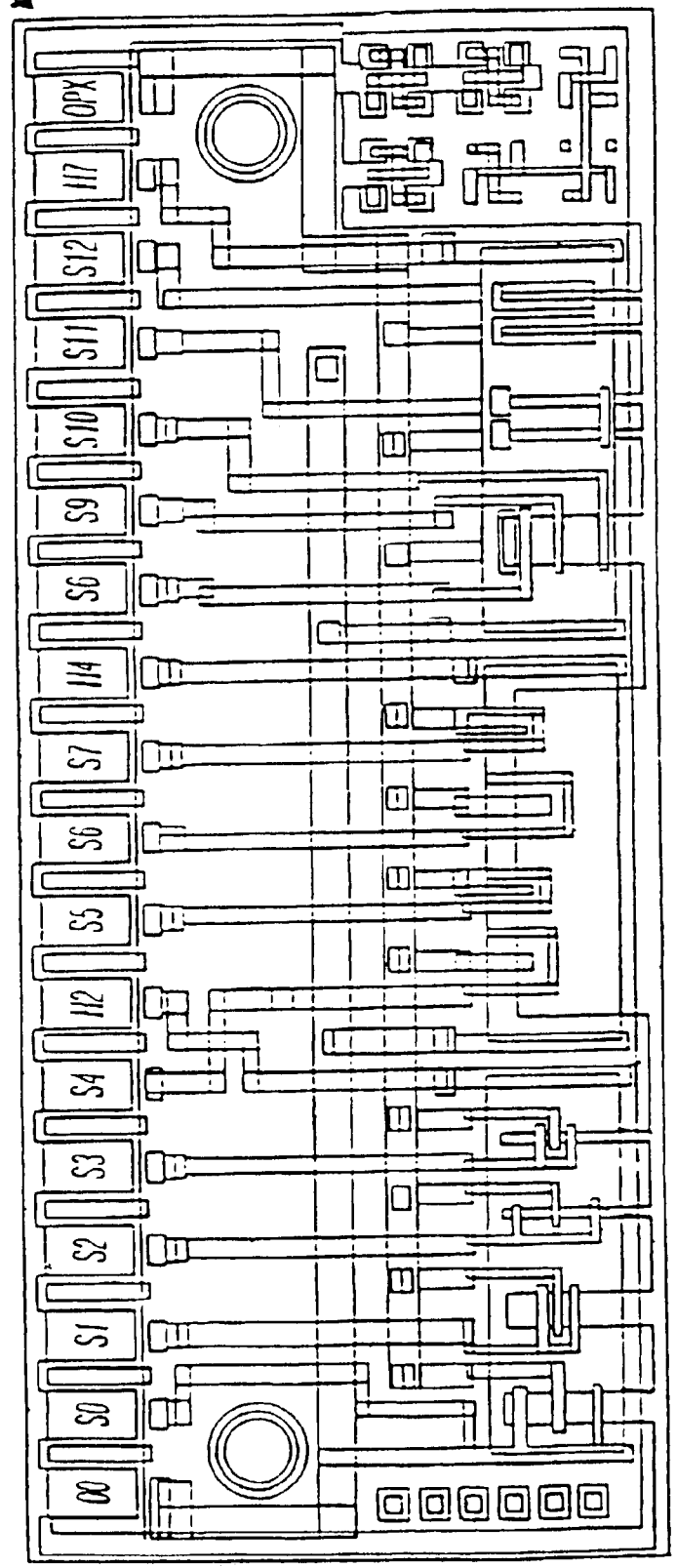
FIG. 1 is an illustration of a gas sensor chip, which can be utilized as the sensor for the present invention.

The present invention provides a method and apparatus for detecting tobacco smoke in exhaled breath. The smoke vapor is detected by devices including but not limited to electronic noses, spectrophotometers (to detect the vapor's IR, UV, or visible absorbance as well as fluorescence) or mass spectrometers (to detect the vapor's characteristic mass display).

The exhaled breath tobacco smoke detector of the present invention will determine the exposure of children to environmental tobacco smoke (ETS) (passive smoke, sidestream smoke, second-hand smoke). The device is applicable for a wide range of research related to the effects of vapors from smoking and their complications.

As noted previously, the health risks related to smoking tobacco products are well documented. Unfortunately, these risks are not only related to direct use of tobacco products, but also to passive exposure from ETS. This exposure is particular hazardous to children and has been shown to be responsible for or to exacerbate a large number of childhood illnesses, such as asthma, otitis media, and respiratory infections. Further, children exposed to smoke are more likely to develop cancer and other serious chronic illnesses. Both the Center for Disease Control (CDC) and the American Academy of Pediatrics (AAP) recognize the risks associated with smoke exposure and recommend screening for ETS. The present invention is designed to provide a method and apparatus for screening for ETS.

For the tobacco smoke detector of the present invention, a "library" of signatures are collected so comparison can be made to the exhaled sample, thus determining whether there has been exposure to tobacco smoke.

In the present invention, vapor concentration measurements of smoke vapors (analytes) are made by detecting the adsorption of molecules onto the surface of a SAW sensor coated with a polymer thin film to provide selectivity and sensitivity to different analytes. The sensor detects ETS components, such as benzene, formaldehyde, nicotine, cotinine, carbon monoxide and cyanide derivatives. The SAW is inserted as an active feedback element in an oscillator circuit. A frequency counter measures the oscillation frequency, which corresponds to the resonant frequency of the SAW sensor. The response of the SAW sensor to the analyte is measured as a shift in the resonant frequency of the SAW sensor. This configuration requires an oscillator circuit, the coated SAW sensor, and a frequency counter, all of which may be housed on a small printed circuit board.

Gas Sensor Technology

The preferred sensor technology is based on surface acoustic wave (SAW) sensors that oscillate at high frequencies and respond to perturbations proportional to the mass load of certain molecules in the vapor phase on the sensor surface with a frequency shift that is detected electronically. Usually, an array of sensors (4–6) is used; each coated with a different chemoselective polymer that selectively binds and/or absorbs vapors of specific classes of molecules. The resulting array "signature" is compared against a library of pre-determined substances and interferents and specific compounds are identified. Sensitivity of the arrays is dependent upon of the homogeneity and consistency of the polymer coating.

Specifically, invention preferably utilizes gas sensor technology, such as the commercial devices referred to as "artificial noses" or "electronic noses." An "electronic or artificial nose" is an instrument, which comprises a sampling system, an array of chemical gas sensors with differing selectivity, and a computer with an appropriate pattern-classification algorithm, capable of qualitative and/or quantitative analysis of simple or complex gases, vapors, or odors. Electronic noses have been used mostly in the food, wine and perfume industry where their sensitivity makes it possible to distinguish between grapefruit oil and orange oil and identify spoilage in perishable foods before the odor is evident to the human nose. There has been little medical-based research and application; however, recent examples demonstrate the power of this non-invasive technique. Electronic noses have determined the presence of bacterial infection in the lungs by analyzing the exhaled gases of patients for odors specific to particular bacteria. See Hanson C W, Steinberger H A: The use of a novel electronic nose to diagnose the presence of intrapulmonary infection. *Anesthesiolog*, V87, No. 3A, Abstract A269, September 1997. Also, genitourinary clinics have utilized electronic noses to screen for, and detect bacterial vaginosis success rate as high as 94%. See Chandiok S, et al.: Screening for bacterial vaginosis: a novel application of artificial nose technology. Journal of Clinical Pathology, 50(9):790–1, 1997. Specific bacterial species can also be identified with the electronic nose based on special odors produced by the organisms. See Parry A D et al.: Leg ulcer odor detection identifies betahaemolytic streptococcal infection. Journal of Wound Care, 4:404–406, 1995.

Exhaled breath is used for a variety of medical tests and measurements. Breath detectors for ethyl alcohol are the most familiar. Real-time measurement of end-tidal carbon dioxide concentration (etCO2) is a valuable tool for estimating arterial CO2 concentration. It is routinely used during anesthesia as a surrogate for invasive arterial blood gas measurement. Further, exhaled anesthetic gas concentration is routinely measured, as is oxygen concentration.

Exhaled gas measurements can also be used diagnostically. *Helicobacter pylori* can be detected by a breath test for ammonia, as can bacterial overgrowth of the small bowel and/or stomach. See Perri F. *Diagnosis of Helicobacter pylori infection: which is the best test? The urea breath test.* Dig Liver Dis. 2000;32 Suppl 3:S196–8; and Ganga-Zandzou P S, Vincent P, Michaud L, Guimber D, Turck D, Gottrand F. *13C-urea breath test in children with Helicobacter pylori infection: validity of the use of a mask to collect exhaled breath samples.* Acta Paediatr. 2001;90: 232–3. Numerous other diagnostic breath tests are available, including several for the evaluation of components of tobacco smoke. Most breath tests are expensive, time consuming and must be performed in a laboratories by trained technicians.

Recently, Defense Advanced Research Projects Agency (DARPA) initiated a program to improve landmine detection by sensing the vapors of breakdown products of TNT and other explosives released into the soil and air. The initiative resulted in several technologies designed to mimic the olfactory system (artificial nose) (http://www.darpa.mil/ato/programs/uxo/index.html). Presently, dogs are used for landmine detection due to their ability to locate extremely low concentrations of these breakdown products. Thus, the program has been named the dog's nose project. Among the competing technologies, some were capable of detecting breakdown products in the range of parts per trillion.

One technology for detection is based on the ability of volatile compounds to cause perturbations in the oscillation of surface acoustic wave (SAW) sensors. See Wohltjen, H.; et al.; "Surface Acoustic Wave Devices for Chemical Analysis", Analytical Chemistry, Vol. 61, pp. 704A; and Fang, M.; et al.; "Detection of Organic Chemicals by SAW Sensor Array", Sensors and Actuators, Vol. B 56 (1999), pp. 155–157. A high degree of sensitivity and specificity can be achieved by coating the surface of the sensors with "chemoselective" polymers that react in a predictable manner with the compound to be detected. See Wohltjen, H.; et al.; "Vapor Detection with Surface Acoustic Wave Microsensors", Chemical Sensors and Microinstrumentation; American Chemical Society, 1989, pp. 157–175; and Wohltjen, et al.; "Determination of Partition Coefficients from Surface Acoustic Wave Vapor Sensor Responses and Correlation with Gas-Liquid Chromatographic Partition Coefficients", Analytical Chemistry, Vol. 60, Num. 9, pp. 869–875. By using an adequate number of sensors and the appropriate polymers, unique "signatures" can be reproducibly detected for specific compounds. Quantitative as well as qualitative measurements are also available.

In the DARPA tests, one version of this technology was able to reliably recognize DNT (a breakdown product of TNT) at levels of 3.5 ppbv in dry air and between 10–15 ppbv in fully saturated air (as is the case for exhaled breath). The range of applicability of this technology to chemical detection is limited only by the ability to develop, discover or design coatings for the SAW device that make it sensitive and selective for the analyte to be measured. When the appropriate coating is available, it is usually possible to detect vapors at the 10–100 ppbv concentration level in a few minutes with selectivity of 1000:1 or more over some commonly encountered interferences. A dynamic range of 3–4 orders of magnitude is common.

A number of patents which describe gas sensor technology include the following: U.S. Pat. No. 5,945,069 to Buchler, for a "Gas sensor test chip"; U.S. Pat. No. 5,918,257 to Mifsud et al., for a "Method and devices for the detection of odorous vapors and applications"; U.S. Pat. No. 4,938,928 to Koda et al., for a "Gas sensor"; U.S. Pat. No. 4,992,244 to Grate, for a "Films of dithiolene complexes in gas-detecting microsensors"; U.S. Pat. No. 5,034,192 to Wrighton et al., for a "Molecule-based microelectronic devices"; U.S. Pat. No. 5,071,770 to Kolesar, Jr., for a "Method for gaseous component identification with #3 polymeric film"; U.S. Pat. No. 5,145,645 to Zakin et al., for a "Conductive polymer selective species sensor"; U.S. Pat. No. 5,252,292 to Hirata et al., entitled "Ammonia sensor"; U.S. Pat. No. 5,605,612 to Park et al., for a "Gas sensor and manufacturing method of the same"; U.S. Pat. No. 5,756,879 to Yamagishi et al., for a "Volatile organic compound sensors"; U.S. Pat. No. 5,783,154 to Althainz et al., for a "Sensor for reducing or oxidizing gases"; and U.S. Pat. No. 5,830,412 to Kimura et al., for a "Sensor device, and disaster prevention system and electronic equipment each having sensor device incorporated therein," all of which are incorporated herein by reference in their entirety.

Recent developments in the field of detection include, but are not limited to, semiconductive gas sensors, mass spectrometers, IR or UV or visible as well as fluorescence spectrophotometers. The vapors change the electrical properties of the semiconductors by varying their electrical resistance. The measurement of these variations provides for the determination of the concentration of substances in the vapors. The methods and apparatus used for detecting vapors use a relatively brief detection time compared to those given by gas chromatography. The SAW sensor devices generally take a few seconds, wherever gas chromatography takes from several minutes to several hours. Other recent gas sensor technologies included in the present invention include apparatus having conductive-polymer gas-sensors ("polymeric"), apparatus having surface-acoustic-wave (SAW) gas-sensors, and aptamers (aptamer biosensors), and amplifying fluorescent polymer (AFP) sensors.

The conductive-polymer gas-sensors (also referred to as "chemoresistors") have a film made of a conductive polymer sensitive to the molecules of vapors. On contact with the molecules, the electric resistance of the sensors change and the measurement of the variation of this resistance enables the concentration of the vapors to be determined. An advantage of this type of sensor is that it functions at ambient temperatures. Further, depending on the chosen conductive polymer, different sensitivities for detecting different vapors can be obtained.

Polymeric gas sensors can be built into an array of sensors, where each sensor is designed to respond differently to different gases and augment the selectivity of the odorous vapors.

The surface-acoustic-wave (SAW) gas-sensors generally include a substrate with piezoelectric characteristics covered by a polymer coating which is able to selectively absorb the vapors. The variation of the resulting mass leads to a variation of its resonant frequency. This type of sensor allows for very good mass-volume measures of the vapors. In the SAW device, the substrate is used to propagate a surface acoustic wave between sets of interdigitated electrodes. The chemoselective material is coated on the surface of the transducer. When a chemical analyte interacts with a chemoselective material coated on the substrate, the interaction results in a change in the SAW properties such as the amplitude of velocity of the propagated wave. The detectable changes in the characteristics of the wave indicate the presence of the chemical analyte.

SAW devices are described in numerous patents and publications, including U.S. Pat. No. 4,312,228 to Wohltjen and U.S. Pat. No. 4,895,017 to Pyke, and Groves W A, et al.: Analyzing organic vapors in exhaled breath using surface acoustic wave sensor array with preconcentration: Selection and characterization of the preconcentrator adsorbent, *Analytica Chimica Acta* 371 (1988) 131–143, all of which are incorporated herein by reference. Other types of chemical sensors known in the art that use chemoselective coatings applicable to the operation of the present invention include bulk acoustic wave (BAW) devices, plate acoustic wave devices, interdigitated microelectrode (IME) devices, and optical waveguide (OW) devices, electrochemical sensors, and electrically conducting sensors.

The operating performance of a chemical sensor that uses a chemoselective film coating is greatly affected by the thickness, uniformity and composition of the coating. For these biosensors, increasing the coating thickness, has a detrimental effect on the sensitivity. Only the portion of the coating immediately adjacent to the transducer substrate is sensed by the transducer. If the polymer coating is too thick, the sensitivity of the SAW device to record changes in frequency will be reduced. These outer layers of coating material compete for the analyte with the layers of coating being sensed and thus reduce the sensitivity of the biosensor. Uniformity of the coating is also a critical factor in the performance of a sensor that uses a chemoselective coating since changes in average surface area greatly effect the local vibrational signature of the SAW device. Therefore, films should be deposited that are flat to within 1 nm with a thickness of 15–25 nm. In this regard, it is important not only that the coating be uniform and reproducible from one device to another, so that a set of devices will all operate with the same sensitivity, but also that the coating on a single device be uniform across the active area of the substrate. If a coating is non-uniform, the response time to analyte exposure and the recovery time after analyte exposure are increased and the operating performance of the sensor is impaired. The thin areas of the coating respond more rapidly to an analyte than the thick areas. As a result, the sensor response signal takes longer to reach an equilibrium value, and the results are less accurate than they would be with a uniform coating.

Most current technologies for creating large area films of polymers and biomaterials involve spinning, spraying, or dipping a substrate into a solution of the macromolecule and a volatile solvent. These methods coat the entire substrate without selectivity and can lead to solvent contamination and morphological inhomogeneities in the film due to non-uniform solvent evaporation. There are also techniques such as microcontact printing and hydrogel stamping that enable small areas of biomolecular and polymer monolayers to be patterned, however, separate techniques like photolithography or chemical vapor deposition are needed to transform these films into microdevices. Other techniques such as thermal evaporation and pulsed laser ablation are limited to polymers that are stable and not denatured by vigorous thermal processes. More precise and accurate control over the thickness and uniformity of a film coating may be achieved by using pulsed laser deposition (PLD), a physical vapor deposition technique that has been developed recently for forming ceramic coatings on substrates. By this method, a target comprising the stoichiometric chemical composition of the material to be used for the coating is ablated by means of a pulsed laser, thereby forming a plume of ablated material that becomes deposited on the substrate.

Polymer thin films, using a new laser based technique developed by researchers at the Naval Research Laboratory (Matrix Assisted Pulsed Laser Evaporation (MAPLE)) have recently been shown to increase sensitivity and specificity of chemoselective Surface Acoustic Wave vapor sensors. A variation of this technique, Pulsed Laser Assisted Surface Functionalization (PLASF) is preferably used to design compound specific biosensor coatings with increased sensitivity for the present invention. PLASF produces similar thin films for sensor applications with bound receptors or antibodies for biosensor applications. High sensitivity and specificity is possible by providing improved SAW biosensor response by eliminating film imperfections induced by solvent evaporation and detecting molecular attachments to specific antibodies.

Certain extremely sensitive, commercial off-the-shelf (COTS) electronic noses, such as those provided by Cyrano Sciences, Inc. ("CSI") (e.g., CSI's Portable Electronic Nose and CSI's Nose-Chip™ integrated circuit for odor-sensing—U.S. Pat. No. 5,945,069—FIG. 1), are preferred in the present invention to monitor the exhaled breath from a patient. The device offers minimal cycle time, can detect multiple odors, can work in almost any environment without special sample preparation or isolation conditions, and do not require advanced sensor design or cleansing between tests.

Other technologies and methods are contemplated herein for detection of vapors. For example, a patient's breath can be captured into a container (vessel) for later analysis at a central instrument such as a mass spectrometer.

Aptamers (aptamer biosensors) may be utilized in the present invention for sensing. Aptamer biosensors are resonant oscillating quartz sensors which can detect minute changes in resonance frequence due to modulations of mass of the oscillating system which results from a binding or dissociation event.

Similarly, amplifying fluorescent polymer (AFP) sensors may be utilized in the present invention for sensing. AFP sensors are an extremely sensitive and highly selective chemosensors that use amplifying fluorescent polymers (AFPs). When vapors bind to thin films of the polymers, the fluorescence of the films decreases. A single molecular binding event quenches the fluorescence of many polymer repeat units, resulting in an amplification of the quenching. Analyte binding to the films is reversible, so the films can be reused.

Figure 2:
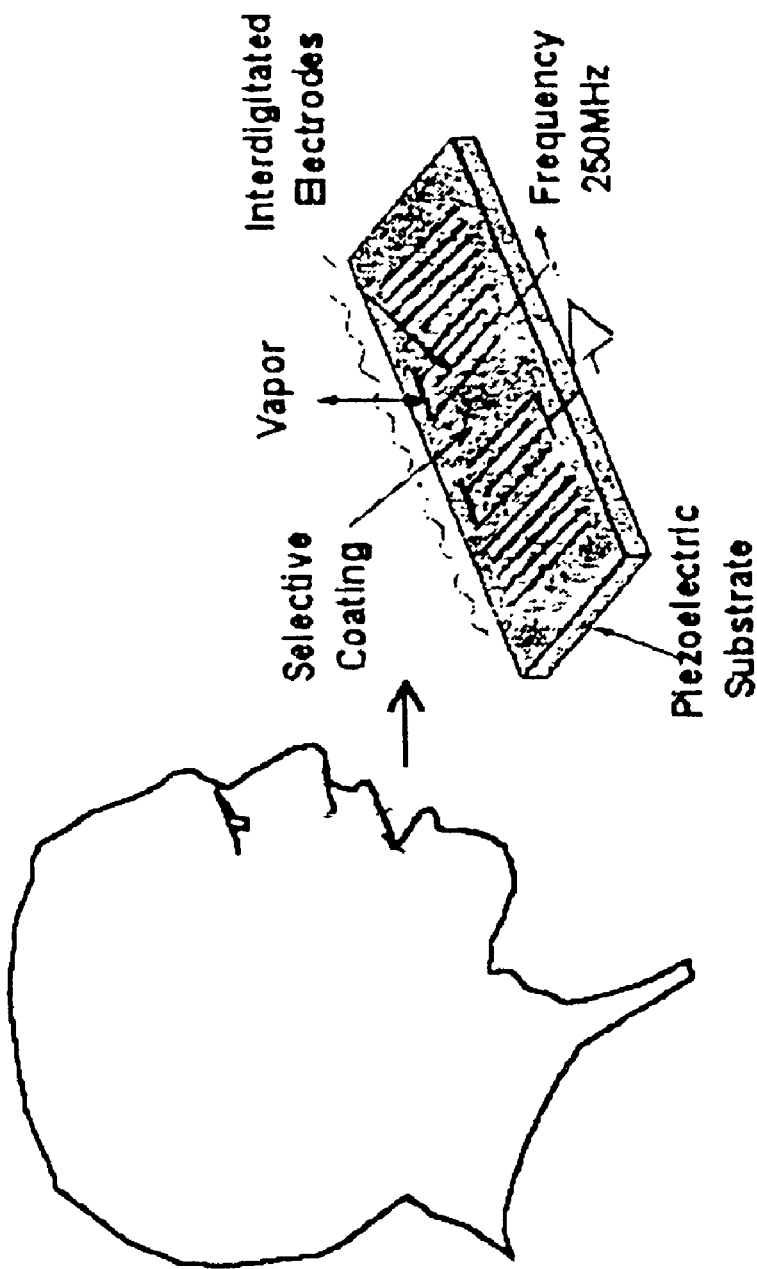
FIG. 2 is an illustration of a chemoselective polymer coated SAW sensor designed for the measurement of exhaled breath in accordance with the present invention.

FIG. 2 is a stylized representation of a chemoselective polymer coated SAW sensor designed for the measurement of exhaled breath vapor.

Figure 3:
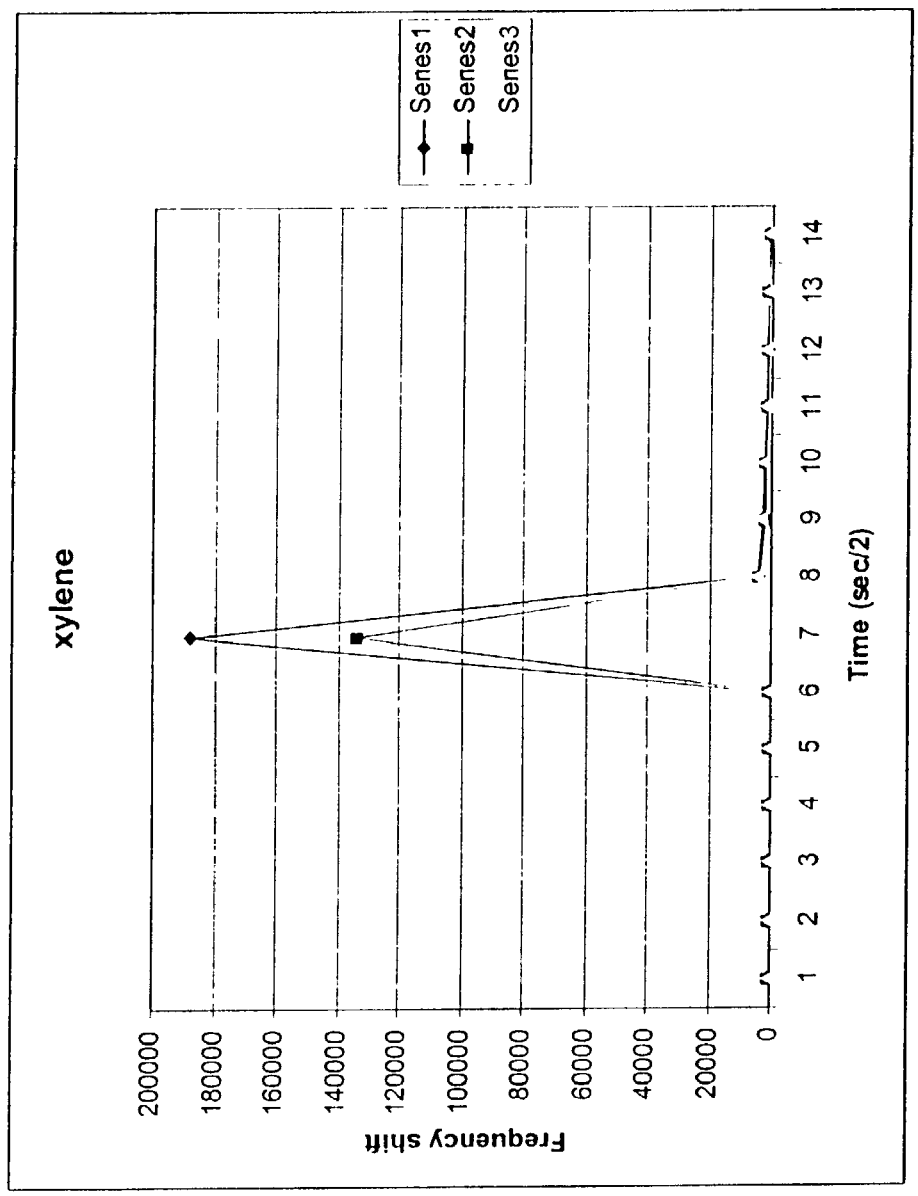
FIG. 3 is a chromatogram for xylene with VaporLab™ with preconcentrator.

FIG. 3 is a chromatogram for xylene with VaporLab™ with preconcentrator. Note that the "signature" has both amplitude and temporal resolution.

In the present invention, vapor concentration measurements (analytes) are made by detecting the adsorption of molecules onto the surface of a SAW sensor coated with a polymer thin film to provide selectivity and sensitivity to different analytes. The SAW is inserted as an active feedback element in an oscillator circuit. A frequency counter measures the oscillation frequency, which corresponds to the resonant frequency of the SAW sensor. The response of the SAW sensor to the analyte is measured as a shift in the resonant frequency of the SAW sensor. This configuration requires an oscillator circuit, the coated SAW sensor, and a frequency counter, all of which may be housed on a small printed circuit board.

Figure 4:
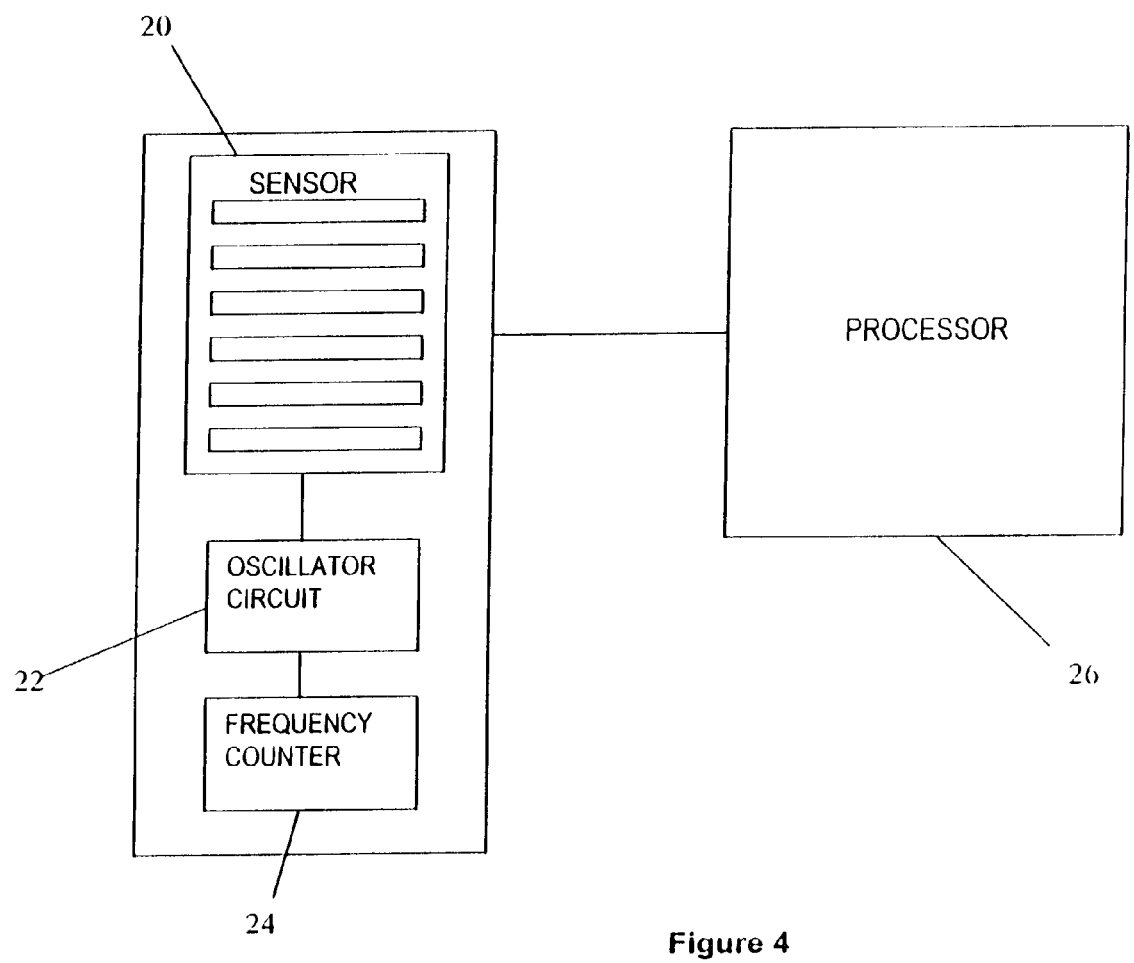
FIG. 4 shows a gas sensor system in accordance with one embodiment of the invention.

FIG. 4 shows an example of a device for detecting a target substance(s) (tobacco smoke) in expired breath having the following components: (a) a surface-acoustic wave sensor 20 capable of detecting the presence of the target substance(s) in expired breath, wherein the sensor responds to the target substance(s) by a shift in the resonant frequency; (b) an oscillator circuit 22 having the sensor as an active feedback element; (c) a frequency counter 24 in communication with the oscillator circuit to measure oscillation frequency which corresponds to resonant frequency of the sensor; and (d) a processor 26 for comparing the oscillation frequency with a previously measured oscillation frequency of the target substance(s) and determining presence and concentration of the target substance(s) therefrom. The sensor can include measuring circuitry (not shown) and an output device (not shown) can also be included (e.g., screen display, audible output, printer).

The processor can include a neural network (not shown) for pattern recognition. Artificial Neural Networks ANNs are self learning; the more data presented, the more discriminating the instrument becomes. By running many standard samples and storing results in computer memory, the application of ANN enables the device to "understand" the significance of the sensor array outputs better and to use this information for future analysis. "Learning" is achieved by varying the emphasis, or weight, that is placed on the output of one sensor versus another. The learning process is based on the mathematical, or "Euclidean," distance between data sets. Large Euclidean distances represent significant differences in sample-to-sample aroma characteristics.

Figure 5:
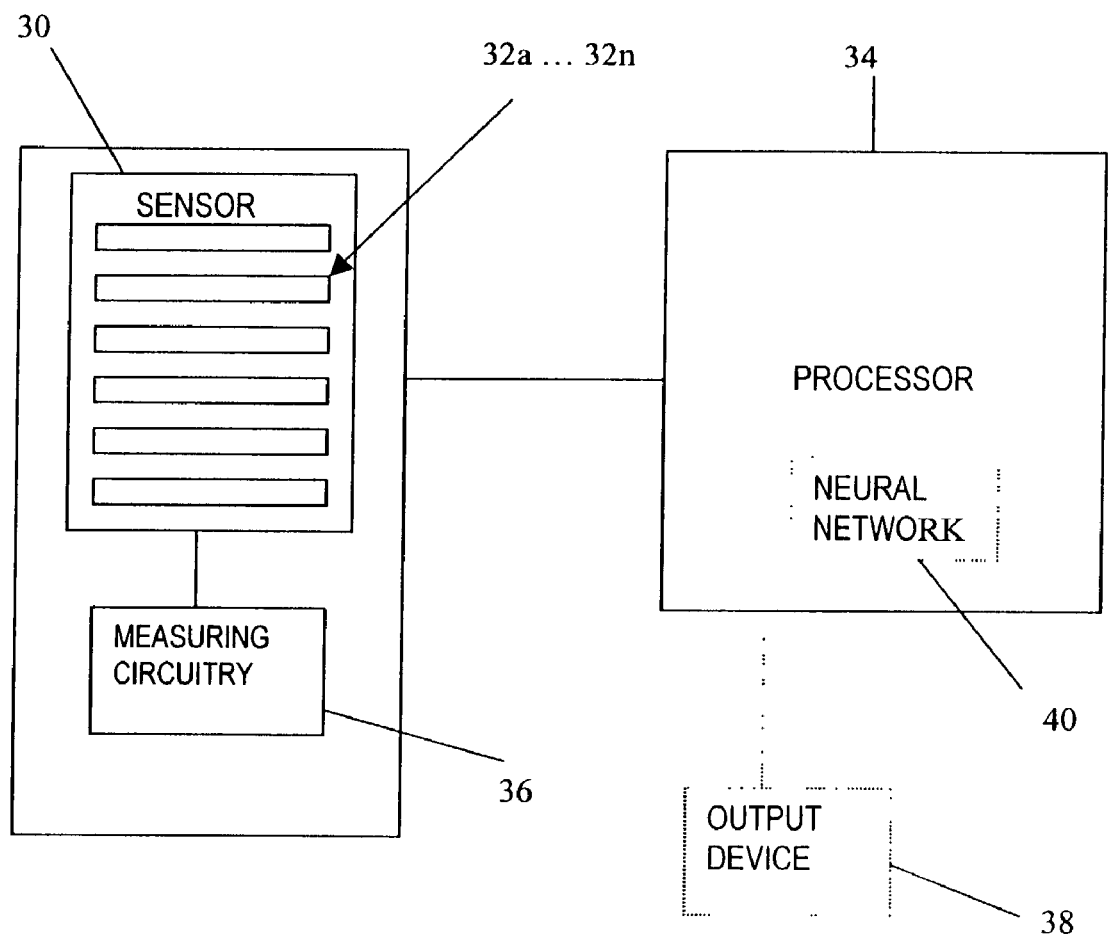
FIG. 5 shows a gas sensor system in accordance with another embodiment of the invention.

In an alternate embodiment, FIG. 5 shows an example of a device for detecting a target substance(s) (tobacco smoke) in expired breath having the following components: (a) a sensor 30 having an array of polymers 32a–32n capable of detecting the presence of the target substance(s) in expired breath, wherein the sensor responds to the target substance(s) by changing the resistance in each polymer resulting in a pattern change in the sensor array; (b) a processor 34 for receiving the change in resistance, comparing the change in resistance with a previously measured change in resistance, and identifying the presence of the target substance(s) from the pattern change and the concentration of the substance(s) from the amplitude. The processor can include a neural network 40 for comparing the change in resistance with a previously measured change in resistance to find a best match (pattern recognition). The sensor can include measuring circuitry 36 and an output device 38 can also be included (e.g., screen display, audible output, printer).

The present invention will determine if a subject has been exposed to vapors by monitoring and analyzing his exhaled breath with the electronic nose. In a preferred embodiment, the device of the present invention is designed so that subjects can exhale via the mouth or nose directly into the device.

Another preferred electronic nose technology of the present invention comprises an array of polymers, (e.g., 32 different polymers), each exposed to a compound. Each of the 32 individual polymers swells differently to the compound creating a change in the resistance of that membrane and generating an analog voltage in response to that specific compound ("signature"). The normalized change in resistance is then transmitted to a processor to identify the type, quantity, and quality of the compound based on the pattern change in the sensor array. The unique response results in a distinct electrical fingerprint that is used to characterize the vapors. The pattern of the array resistance changes is diagnostic of the sample, while the amplitude of the pattern indicates the concentration of the sample.

The responses of the electronic nose to specific vapors fully characterized using a combination of conventional gas sensor characterization techniques. For example, the sensor can be attached to a computer. Marker analysis results can be displayed on the computer screen, stored and/or transmitted. The data analyzer compares the pattern of response to previously measured and characterized responses from known vapors (signatures). Matching the signatures can be performed using a number of techniques, including neural networks. By comparing the analog output from each of the 32 polymers to a "blank" or control, for example, a neural network can establish a pattern which is unique to that substance and subsequently learns to recognize that substance. The particular resistor geometries are selected to optimize the desired response to the particular vapors being sensed. The electronic nose of the present invention is preferably a self-calibrating polymer system suitable for liquid or gas phase biological solutions for a variety of vapors simultaneously.

The electronic nose of the present invention might include integrated circuits (chips) manufactured in a modified vacuum chamber for Pulsed Laser Deposition of polymer coatings. It will operate the simultaneous thin-film deposition wave detection and obtain optimum conditions for high sensitivity of SAW sensors. The morphology and microstructure of biosensor coatings will be characterized as a function of process parameters.

The electronic nose used in the present invention preferably includes a mouthpiece or nosepiece so that patients can exhale directly into the device. The mouthpiece or nosepiece provides for interfacing a patient with the device to readily transmit the exhaled breath to the sensor (See, e.g., U.S. Pat. No. 5,042,501). The output from the neural network of the modified electronic nose should be similar when the same patient exhales directly into the device and when the exhaled gases are allowed to dry before they are sampled by the electronic nose.

The humidity in the exhaled gases represents a problem for certain electronic nose devices, other than SAW sensors, which only work with "dry" gases. When using such humidity sensitive devices, the present invention adapts the electronic nose technology so that a patient can exhale directly into the device by utilizing a means to dehumidify the samples. This is accomplished by including a commercial dehumidifier or a heat moisture exchanger (HME), a device designed to prevent desiccation of the airway during ventilation with dry gases. Alternatively, the patient may exhale through their nose which is an anatomical, physiological dehumidifier that prevent dehydration during normal respiration.

The preferred embodiment of the invention detects the presence of vapors almost immediately in the exhaled breath of the person (or requesting the person to deliberately produce a burp) using the electronic nose. The electronic nose determines their presence as well as their concentration. The electronic noses not only detect different compounds but also compound concentrations.

Preferably, in operation in conjunction with a smoking monitoring program, the electronic nose is used to identify a baseline spectrum for the patient. This proves beneficial for the detection of more than one vapor and possible interference from different foods and odors in the stomach, mouth, esophagus and lungs. The electronic nose can record and/or transmit the data sensed from the patient's breath for monitoring purposes.

A pressure sensor can also be incorporated into the detector to ensure that the patient is actually exhaling into the device. Flow restrictors can also be incorporated to increase the resistance to exhalation. The simple addition of a pressure transducer to the system, allows a pressure change from baseline to be measured during exhalation. Furthermore, a number of detectors are available (i.e., end-tidal carbon dioxide monitors) that can be added to the device.

The electronic nose and/or computer communicating therewith can also notify the medical staff and/or the patient to any irregularities in dosing, dangerous drug interactions, and the like.

REMOTE COMMUNICATION SYSTEM

A further embodiment of the invention includes a communications device in the home (or other remote location) that can be interfaced to the electronic nose. The home communications device is able to transmit, immediately or at prescribed intervals, directly or over a standard telephone line (or other communication means) the data collected by the device. The communication of the data allows the physician the ability to remotely verify the results. The data transmitted from the home can also be downloaded to a computer and stored in a database, and any problems can be automatically flagged (e.g., alarm). Such as system can include features from the system disclosed in U.S. Pat. No. 6,074,345, incorporated herein by reference. Specifically, for example, a pediatric patient with asthma could be sent home with the device and data could be sent at periodic intervals to a healthcare provider.

Following are examples illustratrating procedures for practicing the invention. These examples should be construed to include obvious variations and not limiting.

EXAMPLE 1

Sensor Design for ETS Testing

Purified extracts of ETS components (i.e., benzene, formaldehyde, nicotine, cotinine, carbon monoxide and cynide derivatives) are tested on a Microsensor VaporLab(tm) system which has been optimized for the analytes to be detected. Samples are diluted using a "copper kettle" vaporizer and calibrated gas flow meters, using air as the diluting gas. This allows for calibration curves for each substance to be determined. Using SAW sensors to determine the presence and/or concentration of a particular compound or analyte in a gas sample currently remains an innovative method (i.e., not a standard methodology). In order to ensure the accuracy and integrity of the sensor measurements, the sensor is calibrated both qualitatively and quantitatively with accepted protocol. A headspace autosampler for gas chromatography (GC), in conjunction with a gas mixer, is used to correlate the GC and sensor array responses to different concentrations of the gas samples.

Samples are diluted with an aqueous solution containing an appropriate internal standard and placed into a sealed vial suitable for headspace analysis. The samples along with appropriate standards are incubated at an elevated temperature allowing volatiles to diffuse out of the liquid layer (sample phase) as vapors. These vapors enter into the "headspace" (gas phase) of the sealed vial. Under constant conditions of temperature, pressure and equilibration time, the vapor phase in each of these vials is sequentially sampled and separated on a suitable gas chromatographic capillary column. Volatile components are detected using a flame ionization detector or nitrogen phosphorous detector. Thereafter, the mixed samples of various analytes found in exhaled ETS, if present, are analyzed.

Different brands of cigarettes are purchased and stored in a −20 C freezer until use. Testing is performed on vapors that pass through an Anderson Cascade Impactor (ACI) under laboratory assay conditions maintained at 22.2° C. and 60% relative humidity. Cigarettes are "smoked" according to the Federal Trade Commission standard regimen (puff duration, 2s; interpuff interval, 1 min; puff volume, 35 mL) (Ogg, 1964). Immediately after the cigarette is smoked, filter pads (which capture the smoke particulate fraction) on the 8 stages of the ACI are removed. Each filter pad (stained side facing up) is placed in a clean petri dish and 10-mL of 50:50 methanol:hexane solution is added for 1 hour at ambient temperatureto extract. After extraction, the samples are analyzed by automated headspace gas chromatograph and ETS particulate profiles compared against online ETS vapor chromatograms. ETS byproducts are then identified and quantitated by comparison with standards of known purity. This example, however, is not limited to tobacco smoke as other types of smoke exposure may be tested. For example, health monitoring for firefighters, insinerator operators, and other employees potentially exposed to smoke.

EXAMPLE 2

Diagnostic Software Development

Diagnostic software can identify compounds, and in the case of the detection of tobacco smoke, a library of signatures is recorded to compare with the signatures obtained from the sensor system. Such software includes complex signal processing/neural networks. The system distinguishes analytes from the many interferents that are normally found in exhaled breath. Once the signatures of analytes is known, samples of exhaled breath are taken at various times during the day and on multiple days. These samples are analyzed for interferents and then known concentrations of analytes are added to exhaled breath samples to evaluate the ability of the system to detect the tobacco analytes in the presence of confounding interferents.

Multiple sensors address the broad response of the sensing technology and guarantee selectivity (statistical detection). Statistical pattern recognition divides the full measurement space into a set of regions that are assigned to each class. On the other hand, detection theory recognizes that only part of the measurement space is known, and proposes methods to discriminate among known classes and further between the known classes and the background.

In order to address the sensing of chemicals from the environment, a two stage processing system is used: First, a segmentation stage where the system essentially asks, is there a new chemical? followed by a pattern recognition stage where the system essentially asks given that there is a new chemical, which is it? This is the way statistical detection theory suggests dealing with uncertainty.

Similar concepts are used for chemical sensing. One difference is that in chemical sensing there will be a time series instead of an image. To clarify, the local CFAR (Constant False Alarm Rate) properties are translated in the statistical local variations of the time series, which can be measured by what is referred to as the Generalized Likelihood Ratio Test (GLRT). The GLRT is extended with neural networks to produce a fine segmentation algorithm called competitive mixture of experts. This is the methodology applied to chemical sensing. Basically, the system segments the incoming signal in regions that change statistically from the previous ones. Thus, if the chemical composition in the air does not change the system, it is "called" the background activity. Once there is a statistical change from the previous segment, then the algorithm will segment the nonstationary portion of the time series and presents it to a classifier that identifies it as a suspect vapor (or unknown). This second stage is also based on a neural network classifier. There are several to choose from. A neural topology which implements local decision regions in pattern space is preferable to global discriminants. The new support vector machine (SVM) classifier is preferably applied. As an alternative, a methodology developed in the University of Florida Computational NeuroEngineering Laboratory (CNEL) that finds information relevant features from the data before classification can be used. This method has been also been shown to be very sensitive and specific in real world classification problems. Once the optimal polymers are determined, thin, homogeneously coated SAW sensors are produced using PLASF. This improved polymer deposition technique should optimize the SAW responses to the analytes.

Samples of exhaled breath are collected in non-porous vessels (likely glass) from smoker and non-smokers at specific intervals. In the case of the smokers, the intervals will be from the time of the last cigarette in order to evaluate the time course of the wash-out of specific tobacco smoke components. The collected samples are analyzed as described above. The composition of exhaled tobacco smoke and the rates of disappearance of various components from the breath are temporally analyzed. This technology is used to determine the time course of various components "excretion" with diagnostic potential for evaluating the damage to the lungs and respiratory system based on the duration that various components exist in the exhaled breath. This also has value in forensic pathology as a marker of the time of death.

For example, the time period since death of a human cadaver exposed to tobacco smoke prior to death is determined by: (a) removing a sample of air from the lungs and/or airway of the cadaver; (b) testing the sample by sensor technology for the presence and concentration of components indicative of smoke vapors; (c) correlating the concentration with a previously determined rate of excretion for such components which is indicative of the time since last exposure to tobacco smoke; and (d) determining the time period since death based on the time since last exposure to tobacco smoke. The sensor technology is preferably one of semiconductor gas sensor technology; conductive polymer gas sensor technology; or surface acoustic wave gas sensor technology.

Inasmuch as the preceding disclosure presents the best mode devised by the inventor for practicing the invention and is intended to enable one skilled in the pertinent art to carry it out, it is apparent that methods incorporating modifications and variations will be obvious to those skilled in the art. As such, it should not be construed to be limited thereby but should include such aforementioned obvious variations and be limited only by the spirit and scope of the following claims.

REFERENCES

1. Targeting Tobacco Use: The Nation's Leading Cause of Death. At a Glance 2000 U.S. Department of Health and Human Services. Centers for Disease Control and Prevention.
2. Davis, R M. Moving tobacco control beyond "the tipping point." BMJ 2000; 321: 309–310.
3. Witschi H, Joad J P, Pinkerton K E. The toxicology of environmental tobacco smoke. Annu Rev Pharmacol Toxicol. 1997;37:29–52. Review.
4. Samet J M. Workshop summary: assessing exposure to environmental tobacco smoke in the workplace. Environ Health Perspect. 1999;107 Suppl 2:309–12. Review.
5. Ferrence R, Ashley M J. Protecting children from passive smoking. BMJ 2000;5;321:310–1.
6. Jarvis M J, Goddard E, Higgins V, Feyerabend C, Bryant A, Cook D G. Children's exposure to passive smoking in England since the 1980s: cotinine evidence from population surveys. BMJ 2000; 5;321:343–5.
7. Environmental Tobacco Smoke: A Hazard to Children (RE9716). Pediatrics 1997; 639–642.
8. Villablanca A C, McDonald J M, Rutledge J C. Smoking and cardiovascular disease. Clin Chest Med. 2000; 21:159–72. Review.
9. White J R, Froeb H F, Kulik J A. Respiratory illness in nonsmokers chronically exposed to tobacco smoke in the work place. Chest 1991;100(1):39–43.
10. Kawachi I, Colditz G A. Workplace exposure to passive smoking and risk of cardiovascular disease: summary of epidemiologic studies. Environ Health Perspect. 1999; 107 Suppl 6:847–51. Review.
11. Miller D P, Villa K F, Hogue S L, Sivapathasundaram D. Birth and first-year costs for mothers and infants attributable to maternal smoking. Nicotine and Tobacco Research 2001; 3:25–35.
12. Hovell M F, Zakarian J M, Matt G E, Hofstetter C R, Bernert J T, Pirkle J.Effect of counselling mothers on their children's exposure to environmental tobacco smoke: randomised controlled trial. BMJ 2000;321:337–42.
13. Arborelius E, Hallberg A C, Hakansson A. How to prevent exposure to tobacco smoke among small children: a literature review. Acta Paediatr Suppl. 2000 (434 Suppl):65–70.
14. Toumi T, Johnsson T, Reijula K. Analysis of Nicotine, 3-Hydroxycotinine, Cotinine, and Caffeine in Urine of Passive Smokers by HPLC-Tandem Mass Spectrometry. Clinc. Chem. 1999;45:2164–2172.
15. Etter J F, Vu Duc T, Perneger T V. Saliva cotinine levels in smokers and nonsmokers. Am J Epidemiol. 2000; 151:251–8.
16. Chang M Y, Hogan A D, Rakes G P, Ingram J M, Hoover G E, Platts-Mills T A, Heymann P W. Salivary cotinine levels in children presenting with wheezing to an emergency department. Pediatr Pulmonol. 2000;29:257–63.
17. Hansen A M A M, Garde A H, Christensen J M, Eller N, Knudsen L E, Heinrich-Ramm R. Reference interval and subject variation in excretion of urinary metabolites of nicotine from non-smoking healthy subjects in Denmark. Clin Chim Acta. 2001;304:125–132.
18. Well M A, Johnson J, Jacob P, Benowitz N L. Cotinine in the serum, saliva and urine of non-smokers, passive smokers, and active smokers. Am J Public Health 1988; 78:699–701.
19. Schneider S J, Singer H. Validating reports of nonsmoking with breath and saliva samples: your checkup is in the mail. Add. Behaviors 1983;8:187–191.

20. Perri F. Diagnosis of Helicobacter pylori infection: which is the best test? The urea breath test. Dig Liver Dis. 2000;32 Suppl 3:S196–8.
21. Ganga-Zandzou P S, Vincent P, Michaud L, Guimber D, Turck D, Gottrand F. 13C-urea breath test in children with Helicobacter pylori infection: validity of the use of a mask to collect exhaled breath samples. Acta Paediatr. 2001; 90:232–3.
22. Wohltjen, H.; Ballantine, D. S.; "Surface Acoustic Wave Devices for Chemical Analysis", Analytical Chemistry, Vol. 61, pp. 704A
23. Fang, M.; Vetelino, K.; Rothery, M.; Hines, J.; Frye, G.; "Detection of Organic Chemical by SAW Sensor Array", Sensors and Actuators, Vol. B 56 (1999), pp.155–157
24. Wohltjen, H.; Ballantine, D. S.; Jarvis, N. L.; "Vapor Detection with Surface Acoustic Wave Microsensors", Chemical Sensors and Microinstrumentation; American Chemical Society, 1989, pp. 157–175.
25. Wohltjen, H.; Ballantine, D. S.; Snow, A.; Grate, J. W.; Abraham, M. H.; McGill, A. Sasson, P.; "Determination of Partition Coefficients from Surface Acoustic Wave Vapor Sensor Responses and Correlation with Gas-Liquid Chromatographic Partition Coefficients", Analytical Chemistry, Vol. 60, Num. 9, pp. 869–875
26. Wohltjen, H. Chemical Sensing with Surface Acoustic Wave (SAW) Devices. Microsensor Systems, Inc. (http://www.microsensorsystems.com/pdf/chemicalsensing-.pdf).
27. Bond W S and Hussar D A Detection methods and strategies for improving medication compliance. Am J Hosp Pharm. 1991;48:1978–88.
28. Cramer J A Optimizing long-term patient compliance. Neurology 1995;45(suppl 1);S25-S28.
29. Burman W J, Cohn D L, Reitmeijer C A, et al. Non-compliance with directly observed therapy for tuberculosis. Chest 1997;111:1168–73.
30. Burman W J, Dalton C B, Cohn D L, Butler J R, Reves R R. A cost-effectiveness analysis of directly observed therapy vs self-administered therapy for treatment of tuberculosis. Chest. 1997; 112:63–70.
31. Principe J., Kim M., Fisher J., Target detection in synthetic aperture radar (SAR) using artificial neural networks, IEEE Trans. Image Proc. special issue on neural networks, vol 7, #8, 1136–1149, 1998
32. Principe J., Radisavljevic A., Fisher J., Haytt M., Novak L., Target prescreening based on a quadratic gamma detector, in IEEE Trans. Aerospace, vol 34, #3, 706–715, 1999.
33. Haykin S., Sandberg I., Wan E., Principe J., Fancourt C., Katagiri S., Nonlinear dynamical systems: Feedforward neural network perspective, John Wiley, 2001
34. Principe, J., Xu D., Fisher J., Information Theoretic Learning, in Unsupervised Adaptive Filtering, Simon Haykin Editor, 265–319, Wiley, 2000
35. Principe J., Euliano N., Lefebvre C., Neural Systems: Fundamentals through Simulations, CD-ROM textbook, John Wiley, 2000
36. Zhao Q., Principe J., Brennan V., Xu D., Wang Z., Synthetic aperture radar automatic target recognition with three strategies of learning and representation, Optical Engineering, 39(5), 1230–1244, 2000.
37. Vapnik V. The Nature of Statistical Learning Theory, Springer Verlag, 1998.
38. Zhao Q., Principe J., Forming large margins with support vector machines for synthetic aperture radar automatic target recognition, accepted in IEEE Trans. Aerospace and Elect Systems.

We claim:
1. A method of determining smoke exposure, comprising: obtaining a sample of exhaled breath; and
analyzing said sample of breath with sensor technology to determine the presence of smoke related components thereby determining smoke exposure, wherein the analysis of said sample includes comparing the results sensed in said sample with a predetermined signature profile of a specific smoke related component,
wherein the predetermined signature profile of said specific smoke related component is associated with a chemical selected from the group consisting of: acetaldehyde, acetic acid, acetone, acrolein, 4-Amniobiphenol, ammonia, anatabine, aniline, benzene, benz[a]anthracene, benzo[a]pryrene, benzoic acid, gamma-butyrolactone, cadmium, carbonyl sulfide, catechol, cotinine, cyanide derivatives, dimethylamine, formaldehyde, formic acid, glycolic acid, Harman, hydrazine, hydrogen cyanide, hydroquinone, isoprene, methylamine, methyl chloride, 3-methylpyridine 2-naphthylamino, nickel, nicotine, nitrogen oxides, N-Nitrosodiethanolamine, N-Nitrosodiethylamine, N-Nitrosodimethylamine, NNK, phenol, polonium-210, propionaldehyde, pyridine, quinoline, succinic acid, toluene, 2-Toluidine, 3-Vinylpyridine, xylene, and Zinc.

2. The method of claim 1 wherein said sample is analyzed to determine the presence of said smoke related components by sensor technology selected from the group consisting of: semiconductor gas sensor technology; conductive polymer gas sensor technology; aptamer sensor technology; and amplifying fluorescent polymer (AFP) sensor technology.

3. The method of claim 1 wherein said sample is analyzed to determine the presence of said smoke related components by at least one surface acoustic wave gas sensor produced by technology selected from the group consisting of pulsed laser deposition, matrix assisted pulsed laser evaporation, and pulsed laser assisted surface functionalization.

4. The method of claim 1 wherein the sensor technology produces a unique electronic fingerprint to characterize the smoke exposure such that the presence and concentration of the smoke related components is determined.

5. The method of claim 1 wherein said sample is analyzed to confirm the presence of said smoke related components by a spectrophotometer.

6. The method of claim 1 wherein said sample is analyzed to confirm the presence of said smoke related components by a mass spectrometer.

7. The method of claim 1 further comprising the step of recording data resulting from analysis of said sample.

8. The method of claim 1 further comprising the step of communicating data resulting from analysis of said sample to a remote system.

9. The method of claim 1 further comprising the step of capturing exhaled breath in a vessel prior to analysis.

10. The method of claim 1 further comprising the step of dehumidifying said sample prior to analysis.

11. The method of claim 1 wherein said analysis further includes detecting exhalation with a sensor.

12. The method of claim 11 wherein said sensor is a pressure sensor.

13. The method of claim 1 wherein analysis further includes restricting the flow of exhaled breath with an air flow restrictor.

14. The method of claim 1 wherein the analysis is performed for medical treatment purposes.

15. The method of claim 1 wherein the analysis is performed for research purposes.

16. A method of determining smoke exposure, comprising:
obtaining a sample of exhaled breath;
analyzing said sample of breath with sensor technology to determine the presence of smoke related components thereby determining smoke exposure, wherein said sample is analyzed to determine the presence of said smoke related components by sensor technology selected from the group consisting of: semiconductor gas sensor technology; conductive polymer gas sensor technology; aptamer sensor technology; and amplifying fluorescent polymer (AFP) sensor technology; and
using an oscillator circuit having said sensor technology as an active feedback element.

17. A method of determining smoke exposure, comprising:
obtaining a sample of exhaled breath;
analyzing said sample of breath with sensor technology to determine the presence of smoke related components thereby determining smoke exposure, wherein said sample is analyzed to determine the presence of said smoke related components by sensor technology selected from the group consisting of: semiconductor gas sensor technology; conductive polymer gas sensor technology; aptamer sensor technology; and amplifying fluorescent polymer (AFP) sensor technology;
using an oscillator circuit having said sensor technology as an active feedback element; and
using a frequency counter in communication with said oscillator circuit to measure oscillation frequency which corresponds to resonant frequency of the sensor.

18. A method of determining smoke exposure, comprising:
obtaining a sample of exhaled breath;
analyzing said sample of breath with sensor technology to determine the presence of smoke related components thereby determining smoke exposure; and
analyzing data resulting from analysis of said sample with a neural network classifier.

19. A method of determining smoke exposure, comprising:
obtaining a sample of exhaled breath; and
analyzing said sample of breath with sensor technology to determine the presence of smoke related components thereby determining smoke exposure;
wherein the analysis of said sample includes comparing the results sensed in said sample against a predetermined signature library of interferents.

20. A method of determining smoke exposure, comprising:
obtaining a sample of exhaled breath; and
analyzing said sample of breath with sensor technology to determine the presence of smoke related components thereby determining smoke exposure;
wherein the analysis of said sample includes comparing the results sensed in said sample with a predetermined signature profile of a class of smoke related components.

21. A method of determining smoke exposure by analyzing exhaled breath for the presence of smoke related components, comprising:
obtaining a sample of exhaled breath from a subject who has possibly been exposed to smoke; and
subsequently analyzing said sample using gas sensor technology;
comparing the results of the analysis against a library of known smoke related components and interferents; and
identifying and confirming the presence or absence of smoke related components in said subject.

22. A method of determining subject compliance, comprising:
obtaining a sample of exhaled breath from said subject;
subsequently analyzing said breath sample;
comparing the results of the analysis against a library of known smoke related components and interferents; and
confirming the presence or absence of any smoke related components indicating smoke exposure.

23. The method of claim 22 further comprising the step of identifying a baseline smoke exposure spectrum for said subject prior to exposure to said smoke related components.

24. A method of determining the time course of excretion of at least one smoke related component in expired breath comprising:
obtaining a sample of expired breath at a first interval;
analyzing said sample with sensor technology to determine the concentration of said component;
obtaining at least one additional sample of expired breath at a later interval;
analyzing said additional sample with sensor technology to determine the concentration of said component; and
comparing the concentration of the first sample with the concentration of additional samples to determine the time course of excretion of at least one smoke related component in expired breath.

25. The method of claim 24 further comprising evaluating damage to lungs based on the time course.

26. An apparatus for rapidly determining smoke exposure by analyzing exhaled breath for smoke related components, comprising:
(a) means for receiving exhaled breath from a subject;
(b) means for determining the presence of smoke related components in said breath;
(c) means for reporting results; and
(d) a stored library or specific smoke related components for comparison, wherein said specific smoke related components include at least one of the substances from the group consisting of: acetaldehyde, acetic acid, acetone, acrolein, 4-Amniobiphenol, ammonia, anatabine, aniline, benzene, benz[a]anthracene, benzo[a]pryrene, benzoic acid, gamma-butyrolactone, cadmium, carbonyl sulfide, catechol, cotinine, cyanide derivatives, dimethylamine, formaldehyde, formic acid, glycolic acid, Harman, hydrazine, hydrogen cyanide, hydroquinone, isoprene, methylamine, methyl chloride, 3-methylpyridine, 2-naphthylamine, nickel, nicotine, nitrogen oxides, N-Nitrosodiethanolamine, N-Nitrosodiethylamine, N-Nitrosodimethylamine, NNK, phenol, polonium-210, propionaldehyde, pyridine, quinoline, succinic acid, toluene, 2-Toluidine, 3-Vinylpyridine, xylene, and Zinc.

27. The apparatus of claim 26 further comprising a mouthpiece in communication with the means for receiving exhaled breath.

28. The apparatus of claim 26 further comprising an air flow restrictor in communication with the means for receiving exhaled breath.

29. The apparatus of claim 26 further comprising an air flow sensor in communication with the means for receiving exhaled breath.

30. The apparatus of claim 29 wherein said air flow sensor is a pressure sensor.

31. The apparatus of claim 26 wherein the means for determining the presence of smoke related components in said breath comprises a sensor having a surface exposed to said breath and a material selectively absorptive of a group of chemical substances of which smoke related components are members.

32. The apparatus of claim 31 wherein said sensor comprises a gas sensor.

33. The apparatus of claim 32 wherein said gas sensor is selected from the group consisting of semiconductor gas sensor technology; conductive polymer gas sensor technology; aptamer sensor technology; and amplifying fluorescent polymer (AFP) sensor technology.

34. The apparatus of claim 26 comprising an analysis means, coupled to the sensor, for producing an electrical signal indicative of the presence of said smoke related components.

35. The apparatus of claim 34 further comprising a stored library of interferents for comparison.

36. The apparatus of claim 34 further comprising a stored library of classes of smoke related components for comparison.

37. The apparatus of claim 26, wherein the analysis means are further operative to determine the approximate concentration of said smoke related components.

38. The apparatus of claim 26 further comprising a neural network classifier.

39. The apparatus of claim 26 further comprising means for remotely communicating the results.

40. The apparatus of claim 26 further comprising means for storing the results.

41. A device for detecting at least one target substance in expired breath indicative of smoke exposure comprising:
- a surface-acoustic wave sensor capable of detecting the presence of said target substance in expired breath, wherein said sensor responds to the target substance by a shift in the resonant frequency;
- an oscillator circuit having said sensor as an active feedback element; and
- a frequency counter in communication with said oscillator circuit to measure oscillation frequency which corresponds to resonant frequency of the sensor;
- a processor for comparing the oscillation frequency with a previously measured oscillation frequency of the target substance and determining presence and concentration of the target substance therefrom.

* * * * *

UNITED STATES PATENT AND TRADEMARK OFFICE
CERTIFICATE OF CORRECTION

PATENT NO. : 7,052,468 B2
APPLICATION NO. : 10/153096
DATED : May 30, 2006
INVENTOR(S) : Richard J. Melker and Mark Gold It is certified that error appears in the above-identified patent and that said Letters Patent is hereby corrected as shown below:

Column 3,
Line 8 "benzanthracine, benzopryrene" should read --benz[a]anthracene, benzo[a]pryrene--.

Column 18,
Lines 20-21, "3-methylpyridine 2-naphthylamino" should read --3-methylpyridine, 2-naphthylamine--.

Lines 33-38, Claim 3. Canceled

Column 20,
Line 3, "con firming the presence" should read --confirming the presence--.

Signed and Sealed this

Twenty-first Day of November, 2006

JON W. DUDAS
*Director of the United States Patent and Trademark Office*